(12) United States Patent
Schmidt et al.

(10) Patent No.: US 11,826,243 B2
(45) Date of Patent: Nov. 28, 2023

(54) STENT GRAFT

(71) Applicant: Cook Medical Technologies LLC, Bloomington, IN (US)

(72) Inventors: Martin W. Schmidt, Copenhagen (DK); Bent Oehlenschlaeger, Lille Skensved (DK); Erik E. Rasmussen, Slagelse (DK)

(73) Assignee: Cook Medical Technologies LLC, Bloomington, IN (US)

( * ) Notice: Subject to any disclaimer, the term of this patent is extended or adjusted under 35 U.S.C. 154(b) by 139 days.

(21) Appl. No.: 17/570,620

(22) Filed: Jan. 7, 2022

(65) Prior Publication Data

US 2022/0211482 A1 Jul. 7, 2022

(30) Foreign Application Priority Data

Jan. 7, 2021 (GB) ..................................... 2100184

(51) Int. Cl.
*A61F 2/07* (2013.01)
*A61F 2/95* (2013.01)

(52) U.S. Cl.
CPC .................. *A61F 2/07* (2013.01); *A61F 2/95* (2013.01); *A61F 2002/9511* (2013.01)

(58) Field of Classification Search
CPC .... A61F 2/07; A61F 2/95; A61F 2/954; A61F 2/2439; A61F 2002/072; A61F 2002/075;
(Continued)

(56) References Cited

U.S. PATENT DOCUMENTS 4,878,906 A 11/1989 Lindemann et al.
4,913,141 A 4/1990 Hillstead
(Continued)

FOREIGN PATENT DOCUMENTS

AU 2016/256777 B1 4/2017
EP 2471498 A1 7/2012
(Continued)

OTHER PUBLICATIONS

Kolbel et al, "Staged Proximal Deployment of the Zenith TX2 Thoracic Stent-Graft: A Novel Technique to Improve Conformance to the Aortic Arch," Journal of Endovascular Therapy, vol. 16, 598-602.

(Continued)

*Primary Examiner* — Diane D Yabut
(74) *Attorney, Agent, or Firm* — Crowell & Moring LLP (57) ABSTRACT

Disclosed is a stent graft, including a graft body, a sealing stent at the proximal end of the graft body and completely overlapped by the graft body, and a diameter reducing loop arrangement. The sealing stent includes proximal apices at a proximal end thereof and distal apices at a distal end thereof. The diameter reducing loop arrangement includes a loop element. The loop element includes a first end, a second end, and a strand section from the first end to the second end. The first end is attached to the distal end of the sealing stent. The loop element is configured to pass circumferentially around the distal end of the sealing stent and have a release wire pass through a loop at the second end. The diameter reducing loop arrangement is configured to constrict the distal apices of the sealing stent and cause the sealing stent to adopt a substantially conical or frustoconical shape.

20 Claims, 7 Drawing Sheets

(58) Field of Classification Search
CPC ........ A61F 2002/077; A61F 2002/9505; A61F 2002/9511; A61F 2002/9665; A61F 2220/0075; A61F 2250/001
See application file for complete search history.

(56) References Cited

U.S. PATENT DOCUMENTS

| | | | |
|---|---|---|---|
| 5,693,083 | A | 12/1997 | Baker et al. |
| 5,843,158 | A | 12/1998 | Lenker et al. |
| 6,562,064 | B1 | 5/2003 | deBeer |
| 6,692,521 | B2 | 2/2004 | Pinchasik |
| 6,964,677 | B2 | 11/2005 | Osypka |
| 7,160,318 | B2 | 1/2007 | Greensberg et al. |
| 7,611,528 | B2 | 11/2009 | Goodson, IV et al. |
| 7,803,177 | B2 | 9/2010 | Hartley et al. |
| 7,909,863 | B2 | 3/2011 | Hartley et al. |
| 8,172,895 | B2 | 5/2012 | Anderson et al. |
| 8,348,988 | B2 | 1/2013 | Lad et al. |
| 8,728,148 | B2 | 5/2014 | Roeder et al. |
| 8,926,686 | B2 | 1/2015 | King |
| 8,968,384 | B2 | 3/2015 | Pearson et al. |
| 9,198,787 | B2 | 12/2015 | Kratzberg et al. |
| 9,220,617 | B2 | 12/2015 | Berra |
| 9,278,018 | B2 | 3/2016 | Roeder |
| 9,314,355 | B2 | 4/2016 | Styrc et al. |
| 9,427,307 | B2 | 8/2016 | Pearson et al. |
| 9,498,361 | B2 | 11/2016 | Roeder et al. |
| 9,707,072 | B2 | 7/2017 | King |
| 9,757,263 | B2 | 9/2017 | Roeder et al. |
| 9,855,128 | B2 | 1/2018 | Kölbel et al. |
| 10,172,731 | B2 | 1/2019 | Roeder |
| 10,188,538 | B2 | 1/2019 | Eller et al. |
| 2001/0041925 | A1 | 11/2001 | Konya et al. |
| 2002/0007208 | A1 | 1/2002 | Strecker |
| 2003/0050684 | A1 | 3/2003 | Abrams et al. |
| 2003/0233140 | A1 | 12/2003 | Hartley et al. |
| 2004/0073289 | A1 | 4/2004 | Hartley |
| 2004/0106978 | A1 | 6/2004 | Greenberg et al. |
| 2004/0138734 | A1 | 7/2004 | Chobotov et al. |
| 2004/0193178 | A1 | 9/2004 | Nikolchev |
| 2004/0193244 | A1 | 9/2004 | Hartley et al. |
| 2004/0220655 | A1 | 11/2004 | Swanson et al. |
| 2005/0085890 | A1 | 4/2005 | Rasmussen et al. |
| 2005/0090887 | A1 | 4/2005 | Pryor |
| 2005/0107862 | A1 | 5/2005 | Ohlenschlaeger |
| 2005/0119722 | A1 | 6/2005 | Styrc |
| 2005/0137701 | A1 | 6/2005 | Salahieh et al. |
| 2005/0288768 | A1 | 12/2005 | Sowinski et al. |
| 2006/0142836 | A1 | 6/2006 | Hartley et al. |
| 2006/0190070 | A1 | 8/2006 | Dieck et al. |
| 2007/0043425 | A1 | 2/2007 | Hartley et al. |
| 2007/0088424 | A1 | 4/2007 | Greenberg et al. |
| 2007/0100427 | A1 | 5/2007 | Perouse |
| 2007/0208409 | A1 | 9/2007 | Quigley |
| 2007/0233223 | A1 | 10/2007 | Styrc |
| 2008/0027529 | A1 | 1/2008 | Hartley et al. |
| 2008/0077226 | A1 | 3/2008 | Ouellette |
| 2008/0140178 | A1 | 6/2008 | Rasmussen et al. |
| 2008/0243225 | A1 | 10/2008 | Satasiya |
| 2008/0294234 | A1 | 11/2008 | Hartley et al. |
| 2009/0030497 | A1 | 1/2009 | Metcalf et al. |
| 2009/0082842 | A1 | 3/2009 | Glynn |
| 2009/0082847 | A1 | 3/2009 | Zacharias |
| 2009/0099640 | A1 | 4/2009 | Weng |
| 2009/0112302 | A1 | 4/2009 | Stafford |
| 2009/0171431 | A1 | 7/2009 | Swanson et al. |
| 2009/0204202 | A1 | 8/2009 | Dierking et al. |
| 2009/0259291 | A1 | 10/2009 | Kolbel et al. |
| 2010/0010617 | A1 | 1/2010 | Goodson IV et al. |
| 2010/0168838 | A1 | 7/2010 | Hartley et al. |
| 2010/0211052 | A1 | 8/2010 | Brown |
| 2010/0249896 | A1 | 9/2010 | Sugimoto et al. |
| 2010/0286768 | A1 | 11/2010 | Alkhatib |
| 2010/0324655 | A1 | 12/2010 | Styrc |
| 2011/0087320 | A1 | 4/2011 | Bolduc et al. |
| 2011/0178588 | A1 | 7/2011 | Haselby |
| 2011/0190865 | A1 | 8/2011 | McHugo et al. |
| 2011/0288624 | A1 | 11/2011 | Roeder et al. |
| 2012/0010696 | A1 | 1/2012 | Greenberg et al. |
| 2012/0277848 | A1 | 11/2012 | Roeder et al. |
| 2013/0158648 | A1 | 6/2013 | Hartley et al. |
| 2013/0245743 | A1 | 9/2013 | Norris |
| 2014/0180378 | A1 | 6/2014 | Roeder |
| 2014/0336745 | A1 | 11/2014 | Barthold et al. |
| 2016/0184118 | A1 | 6/2016 | Faber et al. |
| 2016/0199207 | A1 | 7/2016 | Treacy et al. |
| 2016/0278910 | A1 | 9/2016 | Kelly |
| 2018/0125634 | A1 | 5/2018 | King et al. |
| 2018/0311030 | A1 | 11/2018 | Bradway |
| 2019/0091051 | A1 | 3/2019 | Roeder |
| 2022/0160529 | A1 | 5/2022 | Arbefeuille et al. |
| 2022/0192851 | A1 | 6/2022 | Garcia |
| 2022/0211482 | A1 | 7/2022 | Schmidt et al. |

FOREIGN PATENT DOCUMENTS

| | | | |
|---|---|---|---|
| EP | 2604232 | A1 | 6/2013 |
| EP | 3040054 | A1 | 7/2016 |
| EP | 3069696 | B1 | 9/2016 |
| EP | 3187155 | A1 | 7/2017 |
| EP | 3272319 | A1 | 1/2018 |
| EP | 3585306 | A1 | 8/2018 |
| EP | 3395302 | A1 | 10/2018 |
| EP | 3733124 | A1 | 11/2020 |
| GB | 2464978 | A | 5/2010 |
| JP | 2006-346350 | | 12/2006 |
| WO | WO 01/74270 | A2 | 10/2001 |
| WO | WO 2004/017868 | A1 | 3/2004 |
| WO | WO 2004/019823 | | 3/2004 |
| WO | WO 2006/037086 | A1 | 4/2006 |
| WO | WO 2009/126227 | A2 | 10/2009 |
| WO | WO 2010/090699 | A1 | 8/2010 |
| WO | WO 2011/081997 | A1 | 7/2011 |

OTHER PUBLICATIONS

Canadian Office Action and Search Report for CA Application No. 2,737,438 dated August 25, 2015, 3 pages.
Extended European Search Report dated Apr. 4, 2013, pp. 1-7, European Patent Application No. 12197088.3, European Patent Office, The Netherlands.
Examination dated Nov. 25, 2016 for European Patent Application No. 12197088.3, 5 pages.
Notice of Opposition of EP Application No. 187106042. dated Oct. 28, 2021, 7 pages.
European International Search Report and Written Opinion for European Application No. PCT/US2009/005890, dated Dec. 28, 2010, 11 pages.
Office Action for U.S. Appl. No. 13/970,861, dated Jun. 4, 2015, 11 pages.
Response to Office Action for U.S. Appl. No. 13/970,861, dated Oct. 5, 2015, 9 pages
Office Action for U.S. Appl. No. 13/713,517, dated Mar. 16, 2015, 20 pages.
Response to Office Action for U.S. Appl. No. 13/713,517, dated Sep. 16, 2015, 9 pages.
Japanese Office Action and English translation of Japanese Application No. 2011-534517 dated Aug. 21, 2013, 6 pages.
Zenith Alpha TM Thoracic Endovascular Graft Instructions for Use brochure, by Cook Medical, I-ALPHA-THORACIC-442-03, dated Oct. 2017, 16 pages.
Zenith Dissection Endovascular Graft and Stent Device description by Cook Medical, AI-D19767-EN-PA, saved Dec. 16, 2019, 19 pages.
TEVAR (Thoracic Endovascular Aneurysm Repair) Information for Patients and Families, by Liverpool Heart and Chest Hospital, published Jan. 2013, 32 pages.

(56) References Cited

OTHER PUBLICATIONS

Thoracic Endovascular Aortic Repair, Society for Vascular Surgery, https://vascular.org/patients/vascular-treatments/repair-thoracic-aortic-aneurysm/thoracic-endovascular-aortic-repair, saved Jan. 4, 2021, 5 pages.

1. Aortic arch radius of curvature ≥ 20 mm
2. Proximal neck diameter 20-42 mm
3. Proximal neck length ≥ 20 mm
4. Distal neck length ≥ 20 mm
5. Distal neck diameter 20-42 mm
6. Lesser curve
7. Greater curve

FIG. 12

STENT GRAFT

RELATED APPLICATIONS

The present patent document claims the benefit of priority to Great Britain Patent Application No. 2100184.7, filed Jan. 7, 2021, and entitled "Stent Graft," the entire contents of which are incorporated herein by reference.

BACKGROUND

The present invention relates to stent grafts and delivery systems therefor. Aneurysms or ulcers of the descending thoracic aorta or aortic arch can be treated by insertion of a stent graft into an appropriate position. Owing to the curvature of the aorta, it is desirable to try and create conformance of the stent graft with the curve of the aorta, in particular conformance of the proximal end of the stent graft. One known stent graft for doing so includes a proximal alignment stent and a sealing stent distal of the alignment stent. The sealing stent has a suture attached to it for creating better conformance with the curve of the aorta.

SUMMARY OF THE INVENTION

The present invention provides an improved stent graft and/or stent graft delivery system for creating better conformance of the stent graft, in particular the proximal end of the stent graft, with the aorta. In one example, present disclosure provides a stent graft system, including a stent graft having a graft body having a proximal end and a distal end, a sealing stent at the proximal end of the graft body, a majority of the sealing stent being overlapped by the graft body, the sealing stent including proximal apices at a proximal end thereof and distal apices at a distal end thereof, a diameter reducing loop arrangement including at least one diameter reducing loop element, the at least one diameter reducing loop element including a first end, a second end, and a strand section from the first end to the second end, the first end being attached at the distal end of the sealing stent, the at least one diameter reducing loop element being configured to pass circumferentially around the distal end of the sealing stent and have a release wire pass through a loop at the second end, the diameter reducing loop arrangement being configured to constrict the distal apices of the sealing stent and cause the sealing stent to adopt a substantially conical or frustoconical shape.

In another example, a stent graft system is provided, including, a graft body having a proximal end and a distal end, a sealing stent at the proximal end of the graft body completely overlapped by the graft body, the sealing stent including proximal apices at a proximal end thereof and distal apices at a distal end thereof. The system further includes a diameter reducing loop arrangement including at least one diameter reducing loop element, the diameter reducing loop element including a first end, a second end, and a strand section from the first end to the second end, the first end being attached to the distal end of the sealing stent, the diameter reducing loop element being configured to pass at least partially circumferentially around the distal end of the sealing stent and have a release wire pass through a loop at the second end. The diameter reducing loop arrangement is configured to constrict the distal apices of the sealing stent and cause the sealing stent to adopt a substantially conical or frustoconical shape.

"Pass circumferentially around" does not necessarily mean passing circumferentially around the entire circumference. In some embodiments, the at least one diameter reducing loop element is configured to pass circumferentially around only a part of the circumference of the graft body and/or distal end of the sealing stent. In other embodiments the at least one diameter reducing loop element passes circumferentially around the entire circumference of the graft body and/or distal end of the sealing stent. Preferably the at least one diameter reducing loop element is configured to have a release wire pass through the loop externally to the graft body. In one example, the first end of the at least one diameter reducing loop element is attached to the distal end of the sealing stent.

The at least one diameter reducing loop arrangement preferably includes a first diameter reducing loop element and a second diameter reducing loop element, the second diameter reducing loop element including a first end, a second end, and a strand section from the first end to the second end, the first end being attached at the distal end of the sealing stent, for example to the distal end of the sealing stent. The second diameter reducing loop element is configured to pass at least partially circumferentially around the distal end of the sealing stent in the opposite direction to the second diameter first diameter reducing loop element and have the second end of the first diameter reducing loop element pass through a loop at the second end of the second diameter reducing loop element to engage the release wire through both loops at the second ends of the first and second diameter reducing loop elements.

In some configurations, the strand section of the first and/or second diameter reducing loop element is part of a strand which loops back on itself to form the respective loop. The first ends of the first and second diameter reducing loop elements may be preferably attached to adjacent struts of the sealing stent. In one example, the first and second diameter reducing loop elements are configured to pass around the distal end of the sealing stent and overlap every distal apex of the sealing stent.

Each of the first and second diameter reducing loop elements may have a length in the region of from 50% to 75% of an expanded diameter of the graft body. Each of the first and second diameter reducing loop elements may have a length in the region of from 55% to 65% of an expanded diameter of the graft body. Further, every diameter reducing loop element of the diameter reducing loop arrangement contributes to an overall loop arrangement length, the overall loop arrangement length being in the region of from 100% to 150% of an expanded diameter of the graft body. In one example, every diameter reducing loop element of the diameter reducing loop arrangement contributes to an overall loop arrangement length, the overall loop arrangement length being in the region of from 110% to 130% of an expanded diameter of the graft body.

In one preferred embodiment, the first ends of the first and second diameter reducing loop elements are attached to adjacent struts of the sealing stent. In particular the first end of the first diameter reducing loop element is secured or attached to a strut at a distal apex of the sealing stent and the first end of the second diameter reducing loop element is attached to a directly adjacent strut of that distal apex. The first end of the at least one diameter reducing loop element is attached to the distal end of the sealing stent. The first and second diameter reducing loop elements may be configured to pass around the distal end of the sealing stent and overlap every distal apex of the sealing stent.

The strand section of the first and/or second diameter reducing loop element is part of a strand that loops back on itself to form the respective loop. The first and/or second diameter reducing loop element may include a second strand section from the respective second end to the respective first end. The first and/or second strand section of the first and/or second diameter reducing loop element is preferably attached to the sealing stent and/or graft body at a plurality of locations around the circumference of the graft body. And further preferably, the first and/or second strand section of the first and/or second diameter reducing loop element is attached to the sealing stent and/or graft body at the distal apices of the sealing stent. The first and/or second strand section of the first and/or second diameter reducing loop element can be attached to the graft body at a plurality of locations around the circumference of the graft body and/or may be attached to the sealing stent at plurality locations around the circumference of the stent graft body. The first and/or second strand section of the first and/or second diameter reducing loop element is attached to the graft body at a plurality of locations around the circumference of the graft body by penetrating the graft material at each of the plurality of locations. This prevents the diameter reducing loop elements from sliding longitudinally relative to the graft material. Each of the first and/or second diameter reducing loop elements is attached to the graft body and/or sealing stent only at the distal end of the sealing stent The diameter reducing loop arrangement is preferably configured to be actuated by a single release wire, but may include two or more release wires Further, the diameter reducing loop arrangement is configured to be held in a constricting configuration by attachment to a release wire only at a single circumferential location.

The stent graft further includes a distal-most stent and at least one intermediate stent between the sealing stent and the distal-most stent. These stents are preferably free of diameter reducing ties.

The diameter reducing loop arrangement preferably includes a first diameter reducing loop element and a second diameter reducing loop element, the second diameter reducing loop element including a first end, a second end, and a strand section from the first end to the second end, the first end being attached to the distal end of the sealing stent, the second loop diameter reducing element being configured to pass circumferentially around the distal end of the sealing stent in the opposite direction to the first diameter reducing loop element and have the first diameter reducing loop element pass through a loop at the second end of the second diameter reducing loop element, wherein the first ends of the first and second diameter reducing loop elements are attached to adjacent struts of the sealing stent. The first and second diameter reducing loop elements are configured to pass around the distal end of the sealing stent and may overlap every distal apex of the sealing stent. The strand section of each of the first and second diameter reducing loop elements may be part of a strand which loops back on itself to form the respective loop. Each of the first and second diameter reducing loop elements may also included a second strand section from the respective second end to the respective first end. Each of the first and second strand sections of each of the first and second diameter reducing loop elements is attached to the graft body at a plurality of locations, at distal apices of the sealing stent, around the circumference of the graft body, by penetrating the graft material at each of the plurality of locations. Each of the of the first and second diameter reducing loop elements may have a length in the region of from 55% to 65% of an expanded diameter of the graft body, or as set forth above.

The present disclosure also provides a stent graft delivery system, including, the stent graft of the described above, and a release wire, wherein the strand section of the at least one diameter reducing loop element passes circumferentially around the distal end of the sealing stent and passes through the loop at the second end of the at least one diameter reducing loop element, such that the diameter reducing loop arrangement constricts distal apices of the sealing stent and causes the sealing stent to adopt a substantially conical or frustoconical shape.

The stent graft delivery system can include a pre-curved cannula on which the stent graft is retained, wherein the release wire extends within a passageway in a tubing along the cannula, passes out of the passageway in the tubing through a first aperture, passes through the loop at the second end of the first diameter reducing loop element, and passes through a second aperture back into the passageway of the tubing, wherein the release wire is external to the tubing on the outside of the curve of the pre-curved cannula. The tubing is preferably around the cannula such that the passageway in the tubing is in between the tubing and the cannula. However, it is not excluded that the tubing could be the cannula itself and that the passageway could be the lumen of the cannula. As set forth above, the method of deploying a stent graft from the stent graft delivery system includes advancing the stent graft to a deployment site, retracting the release wire from the loop at the second end of the at least one diameter reducing loop element to allow the distal end of the sealing stent to expand.

The present invention also provides a stent graft, having a graft body having a proximal end and a distal end, a sealing stent at the proximal end of the graft body, a majority of the sealing stent is overlapped by the graft body, the sealing stent including proximal apices at a proximal end thereof and distal apices at a distal end thereof, a diameter reducing loop arrangement including first and second diameter reducing loop elements, the first and second diameter reducing loop elements being attached at first ends thereof to directly adjacent struts at a distal apex of the sealing stent, the first and second diameter reducing loop elements passing around the sealing stent in opposite directions, penetrating the graft material at each distal apex of the sealing stent, and meeting at second ends thereof externally to the graft body to be looped around a release wire.

The present invention also provides a stent graft, having a graft body having a proximal end and a distal end, a sealing stent at the proximal end of the graft body and completely overlapped by the graft body, the sealing stent including proximal apices at a proximal end thereof and distal apices at a distal end thereof, a diameter reducing loop arrangement including first and second diameter reducing loop elements, the first and second diameter reducing loop elements being attached at first ends thereof to directly adjacent struts at a distal apex of the sealing stent, the first and second diameter reducing loop elements passing around the sealing stent in opposite directions, penetrating the graft material at each distal apex of the sealing stent, and meeting at second ends thereof externally to the graft body to be looped around a release wire.

The invention can provide an enlarged and modified (as compared to prior art devices) diameter reducing tie suture to generate conformance in the aortic arch in wider spectra of different anatomies. This can decrease the amount of cases where the proximal sealing stent tilts inwards if used in extreme cases.

Further, the invention can reduce tilting of the sealing because the diameter reducing loop arrangement is not dependent on the position of a cannula. In particular, in embodiments of the invention, the constriction is provided by a circumferential arrangement rather than by radial ties to an inner cannula.

BRIEF DESCRIPTION OF THE DRAWINGS

The invention is by way of example only, with reference to the accompanying drawings.

DETAILED DESCRIPTION OF THE DRAWINGS AND THE PRESENTLY PREFERRED EMBODIMENTS

In this description, when referring to a delivery system, the term distal is used to refer to an end of a component which in use is furthest from the surgeon during the medical procedure, including within a patient. The term proximal is used to refer to an end of a component closest to the surgeon and in practice in or adjacent an external manipulation part of the delivery system.

On the other hand, when referring to a stent graft, the term proximal refers to a location which in use is closest to the patient's heart, in the case of a vascular implant, and the term distal refers to a location furthest from the patient's heart.

One problem which has been identified by the inventors is that, in some instances of implanting a stent graft into the aorta, especially if the stent graft is used in extreme cases, the proximal sealing stent can tilt inwards or proximally. As described below, embodiments of the present invention are able to reduce tilting of the sealing stent using a diameter reducing loop arrangement as described. In particular, as described below, embodiments of the invention are able to generate a cone shape for the proximal sealing stent in a manner which is less dependent on the position of the cannula, allowing the proximal sealing stent to deploy in a more angular position, leading to a better conformance in the aortic curve. The diameter reducing loop arrangement described here can reduce proximal tilt of the sealing stent particularly in straight aorta sections.

Figure 1:
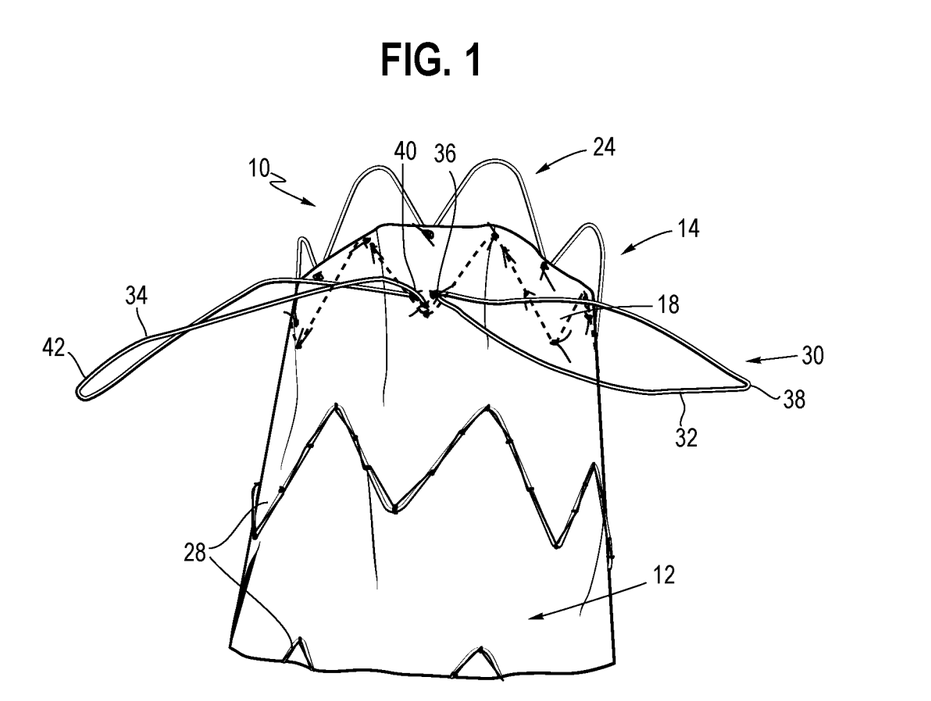
FIG. 1 is a view of a proximal end of a stent graft according to an embodiment of the invention.
Figure 5:
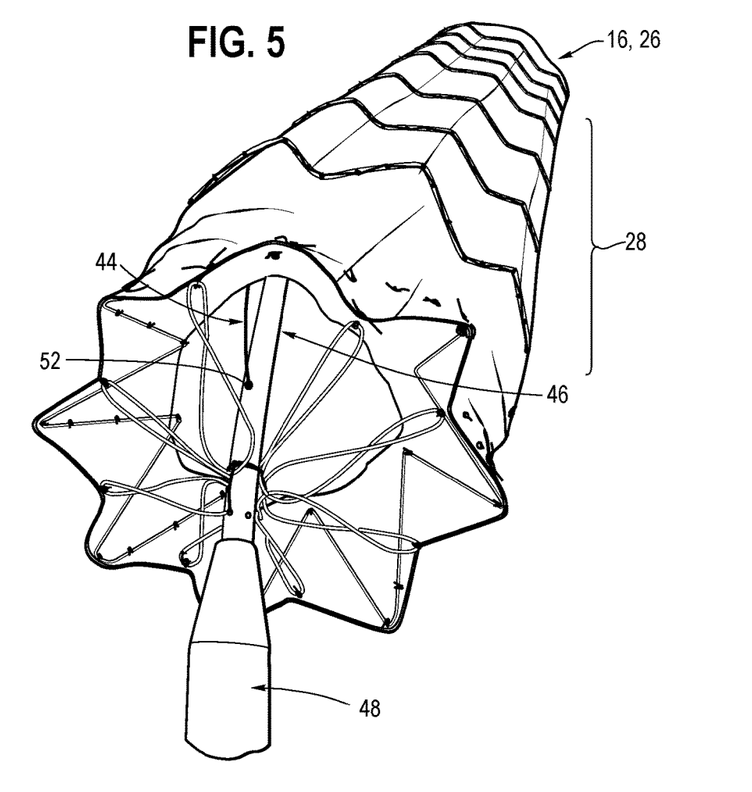
FIG. 5 is a perspective view of the stent graft of the embodiment of FIGS. 1 to 4.

Referring to the Figures, FIG. 1 shows a part of a stent graft 10. The stent graft 10 includes a cylindrical graft body 12 having a proximal end 14 and a distal end 16 (the distal end is shown in FIG. 5). The graft body in this embodiment is constructed of a woven polyester fabric, but other suitable materials can be used in other embodiments.

Stent graft 10 includes a sealing stent 18 at the proximal end of the graft body 12 attached to the graft body 12 and completely overlapped by the graft body 12. It is noted that the term 'overlap' is not intended to imply a relative radial position; an element can be overlapped on the radially internal or external side, or on a combination of radial internal and external. In the embodiment shown in the figures, the sealing stent is an internal stent and is externally overlapped by the graft body 12. However, in other embodiments, the sealing stent can be an external stent and can be internally overlapped by the graft body 12.

Figure 2:
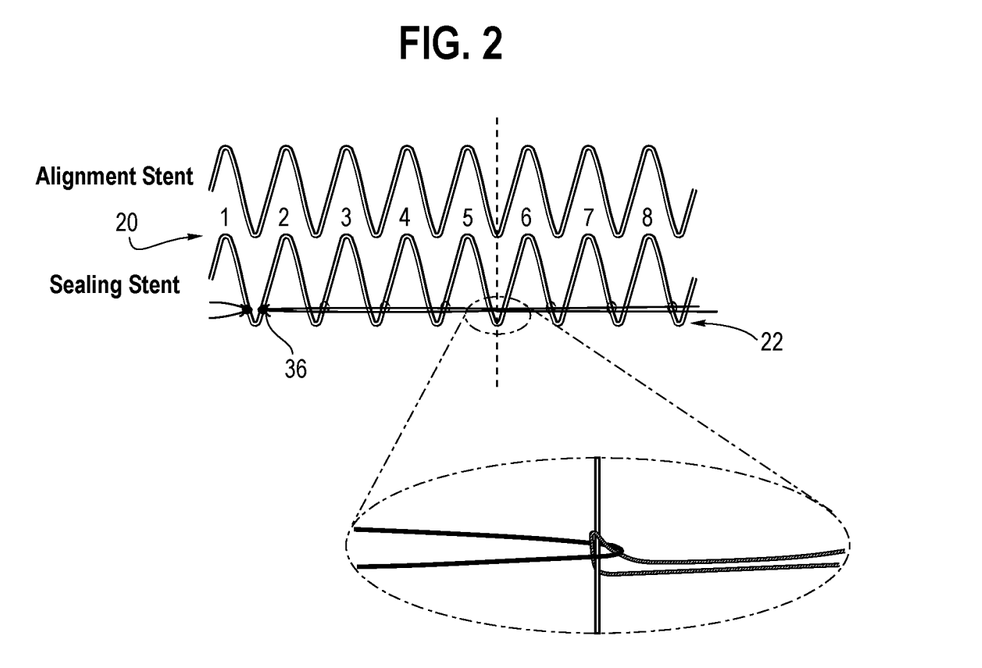
FIG. 2 is a schematic diagram of the diameter reducing loop arrangement of the embodiment of FIG. 1.
Figure 3:
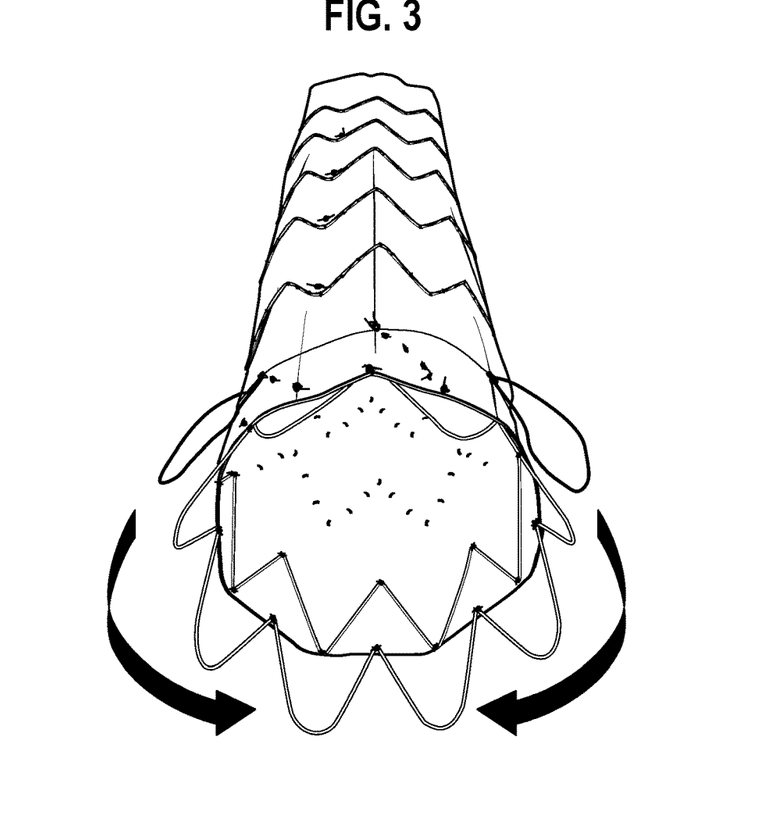
FIG. 3 is a perspective view of the stent graft of the embodiment of FIGS. 1 and 2.

The sealing stent includes proximal apices 20 at a proximal end thereof 20 and distal apices 22 at a distal end thereof (labelled in FIG. 2).

In the embodiment shown in the figures the sealing stent 18 comprises barbs in a conventional manner to improve fixation, although this is not necessary in every embodiment. In this embodiment the barbs protrude through the graft body because the sealing strut is internal.

In the embodiment shown in the figures, the stent graft also includes an alignment stent 24 at the proximal end of the graft body 12. The alignment stent 24 is not completely overlapped by the graft body 12, but extends proximally of the graft body 12, providing a partially exposed or bare stent. In this embodiment, the alignment stent is attached to the graft body 12 only at its distal apices. In this embodiment, the proximal apices of the alignment stent have a greater radius of curvature than the distal apices. It is noted that it is not necessary to have an alignment stent in every embodiment. Also, it is not necessary for the sealing stent to be completely overlapped by the graft body 12 in all embodiments; however, at least a majority of the sealing stent is overlapped by the graft body 12.

The stent graft 10 includes a distal-most stent 26 (shown in FIG. 5) which is completely overlapped by the graft body 12, or of which at least a majority is overlapped by graft body 12. The stent graft also includes a plurality of intermediate stents 28 attached to the graft body 12 between the sealing stent 18 and the distal most stent 26 such that the graft body is fully stented to provide stability and expansile force to open the lumen of the graft body during deployment. The intermediate stents 28 are spaced from each other and from the sealing and distal-most stents longitudinally along the length of the graft body 12. In the embodiment shown in the figures, the distal-most stent and the intermediate stents are external stents. However, in other embodiments they can be internal stents, or some can be internal and some can be external.

As can be seen, all of the stents extend around the circumference of the stent graft in a zig-zag configuration, alternating between proximal and distal apices with each proximal apex connected to each of its neighbouring distal apices by a generally straight portion.

In this embodiment the stents are self-expanding nitinol stents and the attachment is by being sewn to the graft body with braided polyester and monofilament polypropylene suture. However, other materials and forms of attachment can be used in other embodiments. In some embodiments, the stents can be balloon expandable.

In the embodiment shown in the figures, the stent graft 10 is not tapered. However, in other embodiments it can be tapered. In tapered embodiments, the proximal end 14 has a first diameter and the distal end 16 has a second diameter which is less than the first diameter. In tapered embodiments, the stent graft preferably includes a proximal section with the first diameter, a distal section with the second diameter, and a tapered section between the proximal and distal sections, meaning that the stent graft is tapered for only part of its length. Note of course that these diameters for the stent graft refer to an expanded configuration.

Typical (expanded) diameters for the stent graft 10 in non-tapered embodiments, or for the first diameter in tapered embodiments, are in the range of 40 mm to 46 mm. However, other diameters can be used in other embodiments in dependence on the patient and the procedure.

Figure 10:
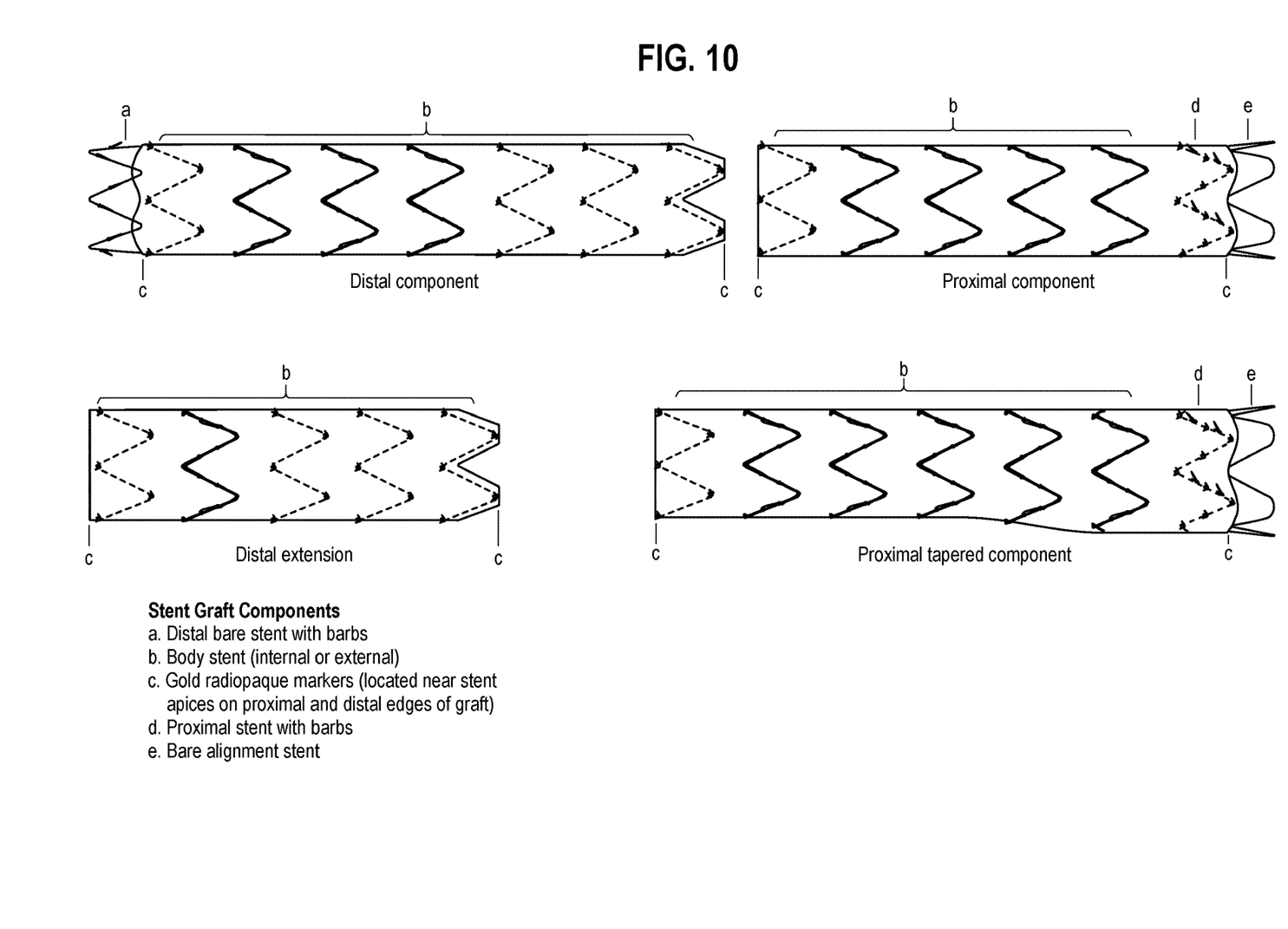
FIG. 10 shows proximal and distal components for different types of Zenith Alpha Thoracic Endovascular Grafts.
Figure 11:
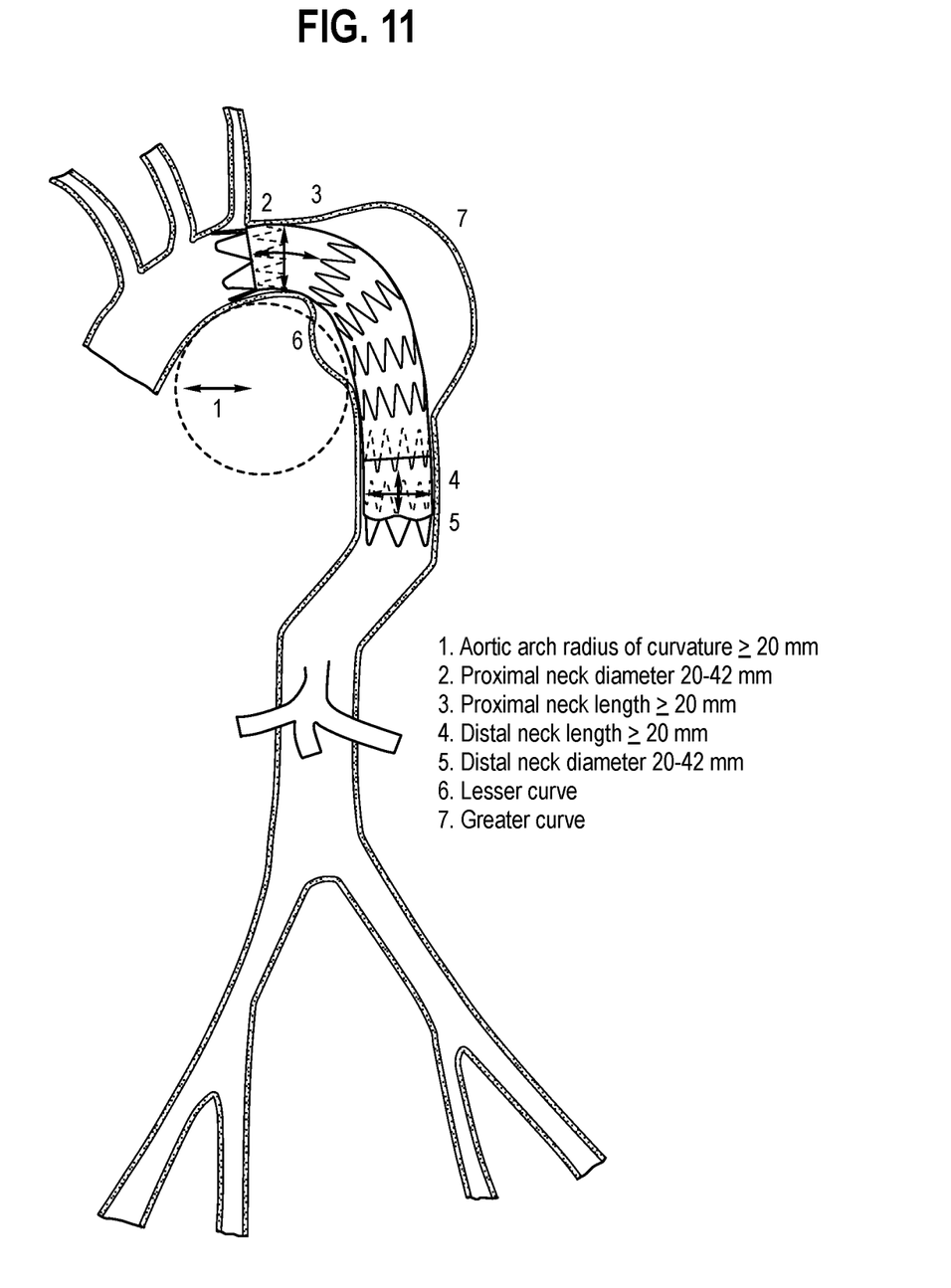
FIG. 11 shows an example of the implantation of a Zenith Alpha Thoracic Graft.

The dimensions, materials, configuration, and deployment procedure for the graft body 12 and stents attached thereto can, except where otherwise indicated, be as for the Zenith Alpha Thoracic Proximal Grafts, available from Cook®, for example those with product numbers ZTA-P-XX-YY or ZTA-PT-XX-YY. Examples of Zenith Alpha Thoracic Proximal Grafts can be seen in FIG. 10 which shows proximal and distal components for different types of Zenith Alpha Thoracic Endovascular Grafts. FIG. 11 shows an example of the implantation of a Zenith Alpha Thoracic Graft.

In the embodiment of FIG. 1, radiopaque markers, in this embodiment gold markers, are placed on stent apices at the proximal and distal aspects of the graft margins denoting the edge of the graft material, to assist with deployment accuracy, although this is not necessary in every embodiment.

The stent graft 10 includes a diameter reducing loop arrangement 30 to reduce the diameter around the distal end of the sealing stent 18 to lead to an angled position or conical configuration of the sealing stent. The diameter reducing loop arrangement 30 comprises a first diameter reducing loop element 32 and a second diameter reducing loop element 34. The first diameter reducing loop element 32 includes a first end 36 and a second end 38. The first diameter reducing loop element 32 includes a strand section from the first end 36 to the second end 38. The first diameter reducing loop element 32 includes a loop at the second end 38. In the embodiment shown in the figures, the first diameter reducing loop element consists of a single strand which passes from the first end 36 to the second end 38 where it loops back on itself to the first end 36, thereby forming a loop at the second end 38. In this way, the first diameter reducing loop element 32 includes a first strand section from the first end 36 to the second end 38 of the first diameter reducing loop element 32 and a second strand section from the second end 38 to the first end 36 of the first diameter reducing loop element 32. However, in other embodiments, the first diameter reducing loop element can include a loop at the second end 38 without the strand section necessarily being part of a single strand which loops all the way back to the first end 36. For example, the strand can be tied to itself at a point between the first and second ends 36, 38, for example by the second strand section extended from the second end 38 and being tied to the first strand section between the first and second ends 36, 38 of the first diameter reducing loop element 32.

The first end 36 of the first diameter reducing loop element is attached at the distal end of the sealing stent 18, for example to the distal end of the sealing stent 18, although in other embodiments it can be attached to the graft body. In the embodiment shown in the figures, the first end 36 of the first diameter reducing loop element 32 is tied to the sealing stent 18 with a knot at a first distal apex of the sealing stent 18. Furthermore, in the embodiment shown in the figures, owing to the fact that the strand of the first diameter reducing loop element loops all the way back to the first end 36, both ends of the strand are tied to the sealing stent 18 at the first distal apex of the sealing stent 18. In particular, the first end 36 of the first diameter reducing loop element 32, and therefore both ends of the strand of the first diameter reducing loop element 32, are tied to a strut or leg of the sealing stent at the first distal apex. The second diameter reducing loop element 34 includes a first end 40 and a second end 42. The second diameter reducing loop element 34 is similar to the first diameter reducing loop element 32 already described.

The second diameter reducing loop element 34 is attached at the distal end of the sealing stent, for example to the distal end of the sealing stent, in the same manner as described above for the first diameter reducing loop element 32, although, as for the first loop element 32, in other embodiments the first end of the second loop element 34 can be attached to the graft body. In the embodiment shown in the figures the second diameter reducing loop element 34 is attached at the first distal apex, which is the same apex to which the first end 36 of the first diameter reducing loop element 32 is attached. In other embodiments, it is possible for the first ends 36, 40 of the first and second diameter reducing loop elements 32, 34 to be attached at different apices, but this would provide less effective diameter restriction.

In the embodiment shown in the figures, the first ends 36, 40 of the first and second diameter reducing loop elements 32, 34 are attached to directly adjacent struts at the first distal apex of the sealing stent 18. In other words, each is attached to the same stent leg, but on each side of the apex. This can be seen in FIGS. 1 and 2.

The first and second diameter reducing loop elements 32, 34, in particular the first and second strand sections thereof, are configured to pass or be wrapped circumferentially around the distal end of the sealing stent 18 in opposite directions from the respective first ends 36, 40 such that the second ends 38, 42 of the first and second diameter reducing loop elements 32, 34 can meet in a constricting configuration. The constricting configuration can restrict the diameter of the distal end of the sealing stent. As described below, the second ends 38, 42 can be retained by a release wire in the constricting configuration to maintain a constricted diameter at the distal end of the sealing stent. In the embodiment shown in the figures, the first and second diameter reducing loop elements 32, 34, in particular the strand sections thereof, are between them configured to pass around the entire circumference of the graft body 12 at the distal end of the sealing stent 18 in the constricting configuration. Each of the first and second diameter reducing loop elements 32, 34 is configured to pass circumferentially around a part of the circumference of the graft body 12 at the distal end of the sealing stent 18 in the constricting configuration.

In the embodiment shown in the figures, the first and second diameter reducing loop elements 32, 34, in particular the strand sections thereof, pass circumferentially around the distal end of the sealing stent 18 in opposite directions, and overlap each distal apex of the sealing stent 18 which they pass such that between them they overlap every distal apex of the sealing stent.

The size of the diameter reducing loop elements determine the size of the diameter reduction of the distal end of the barbed sealing stent 18 in the constricting configuration and the angle of the conical shape created. The lengths of the diameter reducing loop elements 32, 34 may vary depending on the (expanded) diameter of the stent graft 10 (which may vary for example from a diameter of 40 mm to a diameter of 46 mm as discussed above). For a stent graft with a (expanded) diameter of 46 mm, each of the diameter reducing loop elements 32, 34 typically has a length of about 28 mm. Some other options are given in Table 1 below.

TABLE 1

| Expanded graft diameter (mm) | Length of each of the diameter reducing loop elements 32, 34 (mm) | Combined length of the diameter reducing loop elements 32, 34 (mm) |
| --- | --- | --- |
| 40 | 22 or 24 | 44 or 48 |
| 42 | 24 | 48 |
| 44 | 26 or 28 | 52 or 56 |
| 46 | 28 | 56 |

As can be seen, in preferred embodiments, each of the first and second diameter reducing loop elements has a length in the region of from 50% to 75% of the expanded diameter of the graft body, more preferably in the region of from 55% to 65% of the expanded diameter of the graft body. Furthermore, in preferred embodiments, an overall loop arrangement length (to which every diameter reducing loop element of the diameter reducing loop arrangement contributes and which is the combined length of the diameter reducing loop elements in these embodiments) is in the region of from 100% to 150% of the expanded diameter of the graft body, more preferably in the region of from 110% to 130% of the expanded diameter of the graft body. These dimensions are able to provide an advantageous angle to the conical shape created for the sealing stent. Indeed, the overall loop arrangement length can be selected so as to provide a desired angle to the sealing stent when it is held in a conical or frustoconical shape.

Although Table 1 is based on the assumption that the first and second diameter reducing loop elements are the same length as each other, the skilled person will appreciate that they do not need to be the same length. For example, it is possible to increase the length of one of the diameter reducing loop elements and reduce the length of the other, such that they are not the same length as each other, but such that they retain the same combined length dimension for example as given in Table 1.

The skilled person will appreciate that the values above are lengths for the diameter reducing loop elements rather than for the strands forming the diameter reducing loop elements; the strands forming the diameter reducing loop elements are likely to be significantly longer than the values above if laid out in a straight line without loops.

In the embodiment shown in the figures, the first and second diameter reducing loop elements 32, 34 pass circumferentially around the distal end of the sealing stent 18 in opposite directions, and the strand sections thereof are attached to the graft body and/or the sealing stent 18 at each respective distal apex of the sealing stent 18 which they pass. In other words, at every distal apex of the sealing stent 18, the sealing stent 18 and/or the graft body 12 is attached to one or other of the first and second diameter reducing loop elements 32, 34. In the embodiment shown in the figures, the strand sections of the diameter reducing loop elements are attached to the graft body at each distal apex of the sealing stent 18 which they pass by penetrating the graft material at each of those apices.

Figure 9:
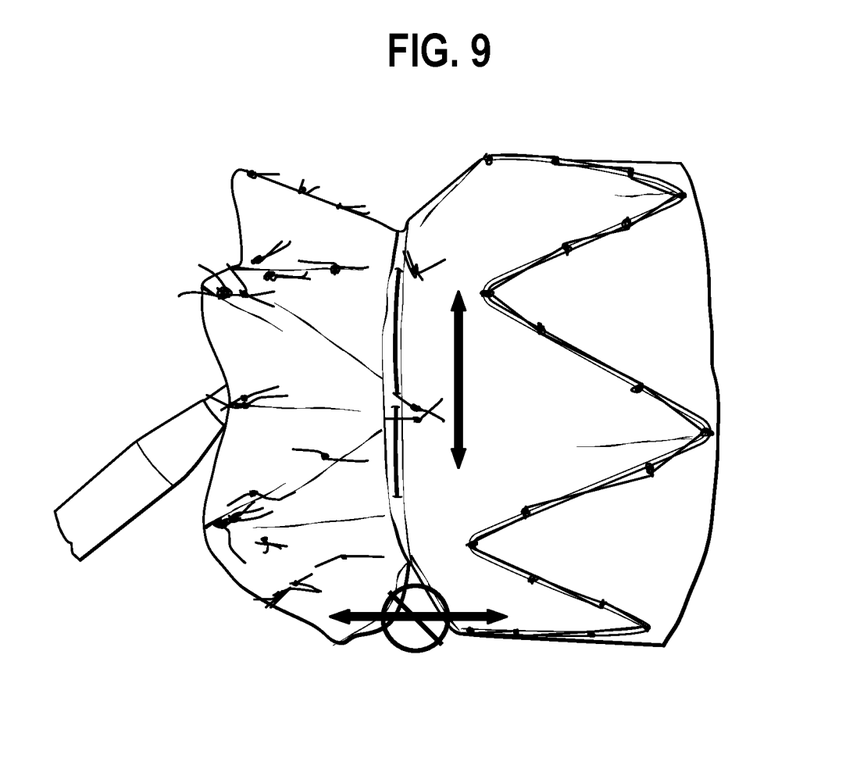
FIG. 9 is a close-up view of the proximal end of the stent graft of the embodiment of FIGS. 1 to 8 showing the restrictions on movement of the diameter reducing loop arrangement.

The attachment of the strand sections of the first and second diameter reducing loop elements to the graft body and/or the sealing stent 18 at each distal apex of the sealing stent 18 which they pass can serve to control the diameter reducing loop elements to prevent them sliding off the distal end of the sealing stent and to make sure the diameter reducing loop elements do not get caught in a barb or knot when released. This can be seen in FIGS. 2 and 6. Furthermore, as can be seen in FIG. 9, as a result of their attachment to the graft body at the distal apices of the sealing stent, the diameter reducing loop elements can only slide in the direction around the graft and not along the length of the graft.

In the embodiment shown in the figures, each of the first and second diameter reducing loop elements 32, 34 passes a set of distal apices of the sealing stent 18 and is attached to the graft body 12 at each of the distal apices of the respective set by the diameter reducing loop element, in particular the strand sections thereof, weaving through the graft material at each of those distal apices. In the embodiment shown in the figures, at each of the distal apices of the respective set, the first and second strand sections of the respective diameter reducing loop element 32, 34 penetrate the graft body 12 and pass from external of the graft body 12 to internal of the graft body 12, pass around one of the struts of the sealing stent 18 at the distal apex and then pass from internal of the graft body 12 to external of the graft body 12. In other words, the strand sections of the diameter reducing loop elements 32, 34 pass radially internally of the graft body 12 around one of the two struts at each distal apex of the respective set of distal apices of the sealing stent 18 but otherwise passes circumferentially around the graft body 12 externally to the graft body 12. Nevertheless, it is possible in other embodiments for the diameter reducing loop elements 32, 34 to be attached to the sealing stent and/or the graft body 12 in a different manner. As can be seen, in the embodiment shown in the figures, each of the first and second loop elements 32, 34 is attached to the graft body and/or sealing stent only at the distal end of the sealing stent.

Of course, in embodiments in which the second strand section does not pass all the way back to the first end of the respective diameter reducing loop element, it may be only the first strand section which passes circumferentially around the distal end of the sealing stent and is attached to the graft body and/or sealing stent at each distal apex of the sealing stent which it passes.

In some embodiments, it is possible to obtain some of the advantages of the attachment of the diameter reducing loop elements at the distal apices by the diameter reducing loop elements being attached at just a subset of the distal apices, although it is preferred that the diameter reducing loop elements are attached at every distal apex as described. Furthermore, in some embodiments it is possible for the diameter reducing loop elements to be substantially unattached to the graft body or sealing stent except at their first ends. However, this is not preferred for the reasons discussed. Furthermore, although in the embodiment shown in the figures the first and second strand sections of each diameter reducing loop element are attached to the graft body and/or the sealing stent at each distal apex of the sealing stent which they pass, in other embodiments just one or other of the strand sections can be so attached. Furthermore, it is not excluded that the first and/or second strand section of the first and/or second diameter reducing loop element can be attached to the sealing stent and/or graft body at a plurality of locations around the circumference of the graft body other than at distal apices of the sealing stent. However, attachment at distal apices is preferable for efficient constriction of the distal end of the sealing stent.

In the constricting configuration, the first and second diameter reducing loop elements 32, 34 together extend around the entire circumference of the graft body 12 and distal end of the sealing stent 18 and the first diameter reducing loop element passes through the loop at the second end 42 of the second diameter reducing loop element, allowing for a release wire to pass through the loop at the second end of the first diameter reducing loop element 32 to hold the first and second diameter reducing loop elements 32, 34 in the constricting configuration. Owing to the location of the first and second diameter reducing loop elements 32, 34 around the distal end of the sealing stent, the diameter reducing loop arrangement 30 is configured to constrict the distal apices of the sealing stent and cause the sealing stent to adopt a substantially conical or frustro conical shape. This conical or frustro conical shape allows the proximal sealing stent to deploy in a more angular position, which leads to a better conformance to the aortic curve.

In the embodiment shown in the figures, the first and second diameter reducing loop elements 32, 34 are made from thread which is green braided PTFE impregnated polyester fibre suture. Other materials can be used in other embodiments; however, the first and second diameter reducing loop elements are preferably each provided by a suture and most preferably by a single strand thereof.

In the embodiment shown in the figures, every intermediate stent is free of diameter reducing ties. However, in other embodiments, one or more intermediate stents may have diameter reducing ties.

The distal-most stent may optionally have a conventional retention arrangement configured to be released in a conventional manner. However, this is not critical and details are therefore not described herein.

Figure 4:
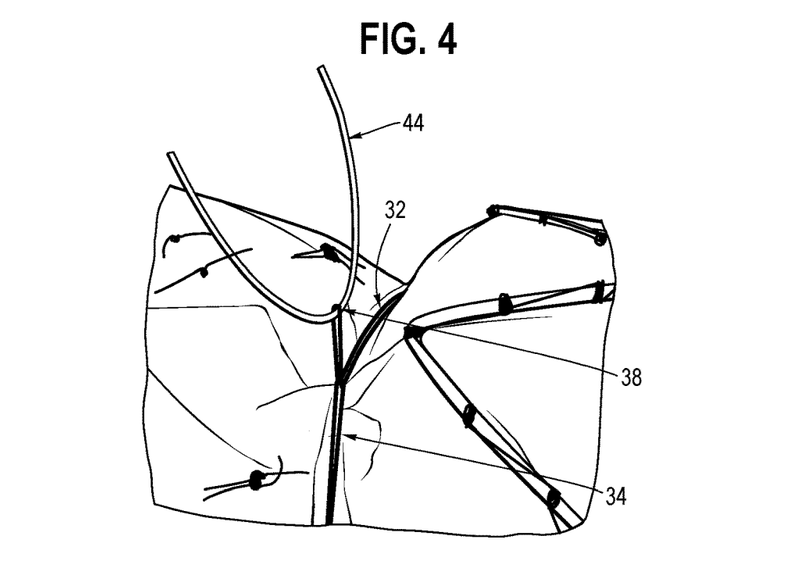
FIG. 4 is a close-up view showing the connection of a release wire in the embodiment of FIGS. 1 to 3.

The stent graft delivery system includes the stent graft and a first release wire 44 (shown for example in FIG. 5). The first release wire 44 passes through the loop at the second end of the first diameter reducing loop element 32 (as shown for example in FIG. 4). As can be seen, the first release wire 44 passes through the loop at the second end of the first diameter reducing loop element 32 externally to the graft body 12. As a result, both the diameter reducing loop elements 32, 34 are attached to the first release wire 44 and each other. They are held by the first release wire in the constricting configuration which pulls the distal apices of the sealing stent radially inwardly and holds the sealing stent in a substantially conical or frustoconical shape, in particular a proximally facing conical or frustoconical shape. The diameter reducing loop arrangement 30 can be released from the constricting configuration by pulling the first release wire 44, which releases the first and second diameter reducing loop elements from each other and allows their respective second ends 38,42 to separate. As a result, the diameter reducing loop elements no longer constrict the diameter of the distal end of the sealing stent 18, which is consequently free to expand.

It is to be noted that in the embodiment shown in the figures, only a single release wire 44 passes through the loop at the second end 38 of the first diameter reducing loop element 32, meaning that the diameter reducing loop arrangement 30 is configured to be actuated by a single release wire. However, in other embodiments, more than one release wire can be used. Nevertheless, it is preferred that the diameter reducing loop arrangement is configured to be held in a constricting configuration by attachment to one or more release wires only at a single circumferential location, to minimise dependence on the position of the cannula.

It is also noted that the first release wire 44 passes through the loop at the second end 38 of the first diameter reducing loop element 32 but not the loop at the second end 42 of the second diameter reducing loop element 34. In other embodiments, it can pass through the loops at the second ends 38, 42 of both the first and second diameter reducing loop elements 32, 34.

In the embodiment shown in the figures, the delivery system includes a delivery cannula 46 including a nose cone 48 at its distal end. In this embodiment, the delivery cannula is compatible with a 0.035 inch wire guide, although other sizes and configurations are possible in other embodiments. The delivery cannula is typically pre-curved in a known manner in order to align appropriately with the aorta at the desired deployment location. The delivery cannula in the embodiment shown in the figures is UAT.

Figure 7:
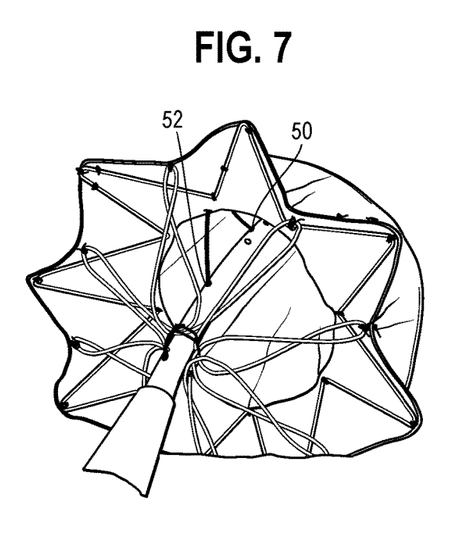
Figure 8:
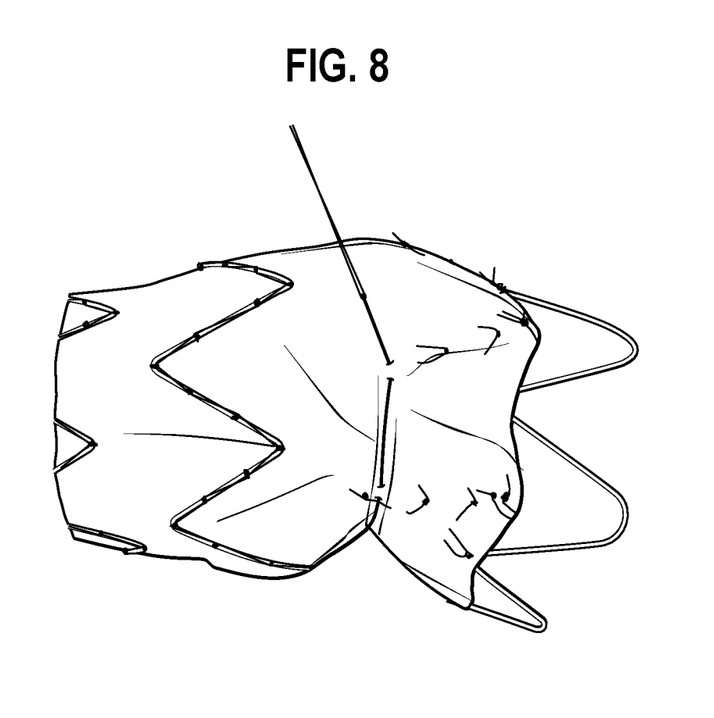
FIG. 8 is a view showing the attachment of the diameter reducing loop arrangement to the stent graft of the embodiment of FIGS. 1 to 7.

The first release wire 44 passes from a release mechanism at the proximal end of the delivery system, through a passageway in between a tubing around the cannula 46 and the outside of the cannula 46 itself. The release mechanism can be any of a variety of configurations provided that it can be actuated to pull the first release wire; in some embodiments it may not be necessary if the first release wire can be pulled directly. The tubing around the delivery cannula 46 includes first and second apertures 50, 52. The stent graft 10 is arranged on the cannula 46 such that the diameter reducing loop arrangement is distal of the first aperture 50 and proximal of the second aperture 52. The first release wire 44 passes out of the passageway of the tubing through the first aperture 50, penetrates the graft body 12 near the distal end of the sealing stent, passes through the loop at the second end 38 of the first diameter reducing loop element 32 external to the graft body 12, goes back through the graft body 12 and through the second aperture 52 into the passageway in the tubing around the cannula 46. As can be seen in FIG. 7, the first release wire 44 penetrates the graft material before and after a distal apex of the sealing stent 18. The first release wire 44 is then temporarily secured within the tubing around the cannula 46 or in the nose cone 48 until it is released by operation of the release mechanism. In this embodiment, the first release wire is external to the tubing around the cannula 46 on the outside of the curve of the pre-curved cannula as shown in FIGS. 5 and 7.

As can be seen from FIG. 7, in the embodiment shown in the figures proximal apices of the alignment stent 24 are constrained in a delivery configuration by a proximal constraining mechanism. In the embodiment shown in the figures, the proximal constraining mechanism is provided by the first 44, as well as second and third release wires constraining the proximal apices of the alignment stent by each emerging through an aperture in the tubing around the cannula 46, looping over a subset of the proximal apices of the alignment stent 24, and entering a further aperture in the tubing around the cannula 46 whereby to constrain the respective subset of the proximal apices to the cannula 46. The subsets constrained by the first, second and third release wires together include all of the proximal apices of the alignment stent such that all of the proximal apices of the alignment stent 24 are constrained. At the proximal end of the delivery system, the first 44, second and third release wires are attached to the release mechanism which may be actuated to retract the first, second and third release wires and thereby release the proximal apices of the alignment stent as well as the diameter reducing loop arrangement. In the embodiment shown in the figures, the release mechanism is configured to retract the first, second and third release wires together; however, in other embodiments it may be possible to retract them separately. Furthermore, other constraining mechanisms for the alignment stent can be used in other embodiments.

As described above, in the embodiment shown in the figures, the first release wire 44 to which the diameter constricting loop arrangement is attached also partially constrains the proximal apices of the alignment stent. However, this is not necessary in every embodiment. In other embodiments, the diameter reducing arrangement 30 may be actuated by a release wire separate from those used to release the proximal apices of the alignment stent and that separate release wire may be actuated by a separate release mechanism.

The delivery system and stent graft described can be used to create proximal conformance and sealing of the stent graft in the aortic arch during thoracic endovascular aortic repair (TEVAR) procedures. For example, the stent graft can be used to treat patients with aneurysms, ulcers or dissections of the descending thoracic aorta or aortic arch.

The graft length is preferably selected to cover the aneurysm, ulcer or dissection as measured along the greater curve of the aneurysm, ulcer or dissection, plus a minimum of 20 mm of seal zone on the proximal and distal ends.

Figure 6:
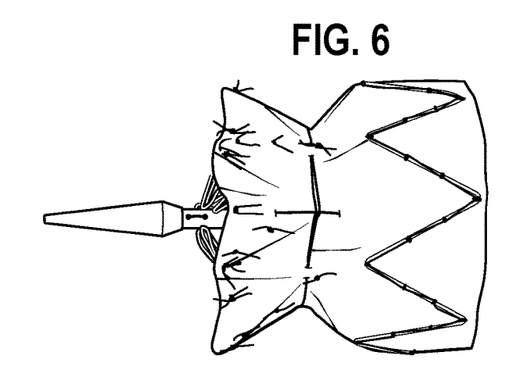
FIGS. 6 and 7 are close-up views of the proximal end of the stent graft of the embodiment of FIGS. 1 to 5.

During introduction, the stent graft is covered by a sheath (not shown) in a known manner. This can for example be a Flexor® Introducer Sheath, which resists kinking and is hydrophilic coated to enhance trackability in the iliac arteries and thoracic aorta, with a Captor® Hemostatic Valve which can be loosened or tightened for the introduction and/or removal of ancillary devices into and out of the sheath. In this embodiment, the introducer sheath is 20 Fr with an outer diameter of 7.7 mm, although different dimensions may be used in other embodiments. The delivery cannula 46 is advanced to the deployment site in a known manner, for example by tracking over a wire guide, such as a stiff 0.035 inch, 260/300 cm LESDC wire guide. The pre-curve of the cannula serves to align the cannula with the vessel with the first release wire external to the tubing around the cannula on the outside of the curve. Once the stent graft 10 is at the desired deployment site, the sheath is retracted in a conventional manner allowing the stent graft 10 to partially expand, leaving the proximal end of the stent graft 10 in the configuration shown in FIG. 6. As can be seen in FIG. 6, the proximal apices of the alignment stent 24 remain constrained against the cannula 46 and the distal end of the sealing stent 18 remains constricted by the diameter constricting loop arrangement 30. As a result, the sealing stent has a conical or frustoconical shape, which is maintained by attachment of the diameter reducing loop elements 32, 34 to the first release wire 44 externally to the graft body 12. As a result, the diameter constraining loop arrangement 30 is not dependent on the position of the cannula 46.

Once the surgeon is satisfied that the stent graft is in the correct position, he or she may retract the release wires. When the release wires are retracted, they are retracted from the proximal apices of the alignment stent, which are thereby allowed to expand. As the first release wire 44 is retracted proximally of the diameter reducing loop arrangement 30, it is retracted from the loop at the second end 38 of the first diameter reducing loop element 32. This releases the first and second diameter reducing loop elements from each other and the first diameter reducing loop element 32 is able to slide out of the loop at the second end 42 of the second diameter reducing loop element 34 and the second ends 38,42 of the first and second diameter reducing loop elements 32, 34 are thereby allowed to separate. As a result, the diameter reducing loop elements no longer constrict the diameter of the distal end of the sealing stent, and the distal apices of the sealing stent can expand into contact with the vessel wall.

Figure 12:
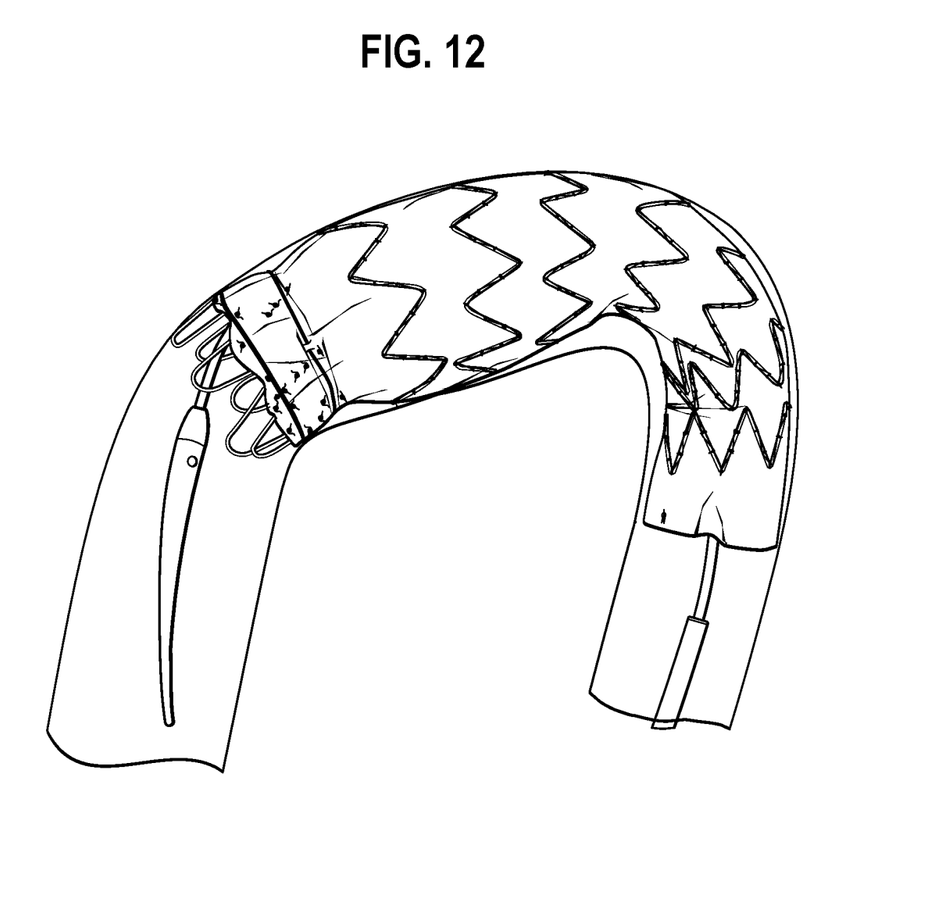
FIG. 12 shows a deployed embodiment of the present invention.

The conical shape of the sealing stent before full deployment, and the independence of the loop arrangement from the position of the cannula 46, means that the proximal sealing stent can deploy in a more angular position which leads to better conformance of the aortic curve and can reduce proximal tilt of the sealing stent for example in straight aorta sections. This is shown in FIG. 12. This can allow the stent graft to be used in wider spectra of different anatomies as the proximal sealing stent is less likely to tilt inwards even if used in extreme cases.

If appropriate for the patient, the stent graft described herein can be used as a proximal component of a modular stent graft together with a distal component, or it can be used independently. The distal component can be for example a Zenith Alpha Thoracic Distal Graft from Cook®. However, other types of distal extensions can of course be used, in particular for example if a dissection is being treated.

In some embodiments, the stent graft can be provided with one or more scallops, fenestrations, internal branches and/or external branches.

Although the embodiment shown in the figures includes first and second diameter reducing loop elements 32, 34, in some embodiments it is possible to use any number of diameter reducing loop elements in the diameter reducing loop arrangement, provided that the diameter reducing loop arrangement is configured to constrict distal apices of the sealing stent to cause the sealing stent adopt a substantially conical or frustro conical shape.

Although release wire(s) extend(s) through a passageway in a tubing around the cannula in the above described embodiment, it is not excluded that it/they could extend in the lumen of the cannula instead, with the corresponding apertures being provided in the cannula itself.

European Application No. 22275002.8 filed on January 27 is co-pending with the present application, the contents of which are incorporated by reference herein in their entirety.

All optional and preferred features and modifications of the described embodiments and dependent claims are usable in all aspects of the invention taught herein. Furthermore, the individual features of the dependent claims, as well as all optional and preferred features and modifications of the described embodiments are combinable and interchangeable with one another.

The invention claimed is:
1. A stent graft system, comprising:
a graft body having a proximal end and a distal end;
a sealing stent at the proximal end of the graft body and at least partially overlapping the graft body, the sealing stent including proximal apices at a proximal end of the sealing stent and distal apices at a distal end of the sealing stent;
a diameter reducing arrangement for reducing the diameter of the distal end of the sealing stent including first and second diameter reducing loop elements, the first diameter reducing loop element having a first end, a second end and a length, the second diameter reducing loop element having a first end, a second end and a length;
wherein the first end of the first diameter reducing loop element is attached to a first strut of a distal apex and the first end of the second diameter reducing loop element is attached to a second strut of the distal apex directly adjacent the first strut;

wherein the lengths of the first and second diameter reducing loop elements extend at least partially circumferentially around the distal end of the sealing stent in opposite directions;

wherein the lengths of the first and second diameter reducing loop elements penetrate the graft material at a plurality of points about the distal end of the sealing stent; and wherein the second ends of the first and second diameter reducing loop elements meet at a point external to the graft body and engage a release wire external to the graft body thereby reducing a diameter of the distal end of the sealing stent such that the sealing stent has a substantially conical or frustoconical shape.

2. The stent graft system of claim 1, wherein the diameter of the distal end of the sealing stent is less than a diameter of the proximal end of the sealing stent.

3. The stent graft system of claim 1, wherein the second end of the first diameter reducing loop element passes through the second end of the second diameter reducing loop element.

4. The stent graft system of claim 1, wherein each of the lengths of the first and second diameter reducing loop elements is from about 50% to about 75% of an expanded diameter of the graft body.

5. The stent graft system of claim 4, wherein each of the lengths of the first and second diameter reducing loop elements is from about 55% to about 65% of the expanded diameter of the graft body.

6. The stent graft system of claim 1, wherein the first and second diameter reducing elements contribute to an overall loop arrangement length, the overall loop arrangement length being from about 100% to about 150% of an expanded diameter of the graft body.

7. The stent graft system of claim 6, wherein the first and second diameter reducing elements contribute to an overall loop arrangement length, the overall loop arrangement length being from about 110% to about 130% of an expanded diameter of the graft body.

8. The stent graft system of claim 1, wherein the sealing stent entirely overlaps the graft body.

9. The stent graft system of claim 8, wherein the sealing stent is internal to the graft material.

10. The stent graft system of claim 1, wherein each of the lengths of the first and second diameter reducing loop elements penetrates the graft material at a plurality of distal apices.

11. The stent graft system of claim 1, wherein the first and second diameter reducing loop elements are precluded from sliding longitudinally relative to the graft material.

12. The stent graft system of claim 1, further including a plurality of stents along the length of the graft material, wherein each of the plurality of stents is free of any diameter reducing loop elements.

13. A stent graft system, comprising:
a graft body having a proximal end and a distal end;
a sealing stent at the proximal end of the graft body and at least partially overlapping the graft body, the sealing stent including proximal apices at a proximal end of the sealing stent and distal apices at a distal end of the sealing stent;
a diameter reducing arrangement for reducing the diameter of the distal end of the sealing stent including first and second diameter reducing loop elements, the first diameter reducing loop element having a first end, a second end and a length, the second diameter reducing loop element having a first end, a second end and a length;

wherein the first end of the first diameter reducing loop element is attached to a first strut of a distal apex and the first end of the second diameter reducing loop element is attached to a second strut of the distal apex directly adjacent the first strut;

wherein the lengths of the first and second diameter reducing loop elements extend at least partially circumferentially around the distal end of the sealing stent in opposite directions;

wherein the lengths of the first and second diameter reducing loop elements penetrate the graft material at a plurality of points about the distal end of the sealing stent;

wherein the second ends of the first and second diameter reducing loop elements meet at a point external to the graft body and engage a release wire external to the graft body thereby reducing a diameter of the distal end of the sealing stent; and wherein each of the lengths of the first and second diameter reducing loop elements is from about 50% to about 75% of an expanded diameter of the graft body.

14. The stent graft system of claim 13, wherein each of the lengths of the first and second diameter reducing loop elements is from about 55% to about 65% of the expanded diameter of the graft body.

15. The stent graft system of claim 13, wherein the first and second diameter reducing elements contribute to an overall loop arrangement length, the overall loop arrangement length being from about 100% to about 150% of an expanded diameter of the graft body.

16. The stent graft system of claim 15, wherein the first and second diameter reducing elements contribute to an overall loop arrangement length, the overall loop arrangement length being from about 110% to about 130% of an expanded diameter of the graft body.

17. The stent graft system of claim 13, wherein the sealing stent entirely overlaps the graft body.

18. The stent graft system of claim 13, wherein the second end of the first diameter reducing loop element passes through the second end of the second diameter reducing loop element.

19. The stent graft system of claim 13, wherein the sealing stent has a substantially conical or frustoconical shape and a diameter of the sealing stent at the distal apices is less than a diameter of the sealing stent at the proximal apices.

20. A stent graft system, comprising:
a graft body having a proximal end and a distal end;
a sealing stent at the proximal end of the graft body and entirely overlapping the graft body, the sealing stent including proximal apices at a proximal end thereof and distal apices at a distal end thereof and a strut extending between each of the proximal and distal apices;
a diameter reducing arrangement at the distal apices of the sealing stent, the diameter reducing arrangement comprising,
a diameter reducing loop including a first looped end, a second looped end, and a strand between the first looped end and the second looped end, the diameter reducing loop extending circumferentially about the distal end of the sealing stent such that the first looped end and the second looped end overlap and engage a release wire external to the graft body through the first and second looped ends, wherein the strand of the diameter reducing loop penetrates the graft material at a plurality of points about the distal end of the sealing stent and constricts the distal end of the sealing stent to a reduce diameter, whereby the sealing stent has a substantially conical or frustoconical shape and a diameter of the sealing stent at the distal apices is less than a diameter of the sealing stent at the proximal apices.

* * * * *